United States Patent [19]
Chen et al.

[11] Patent Number: 5,476,779
[45] Date of Patent: Dec. 19, 1995

[54] DNA ENCODING INSULIN-LIKE GROWTH FACTOR II ISOLATED FROM RAINBOW TROUT

[75] Inventors: Thomas T. Chen, Severna Park; Michael J. Shamblott, Baltimore, both of Md.

[73] Assignee: University of Maryland at College Park, College Park, Md.

[21] Appl. No.: 953,230

[22] Filed: Sep. 30, 1992

[51] Int. Cl.$^6$ .......................... C12N 15/00; C12N 15/17; C12N 15/18

[52] U.S. Cl. .................. 435/240.1; 536/23.51; 435/69.4; 435/240.2; 435/320.1

[58] Field of Search ................. 536/23.5, 23.51; 435/69.1, 240.1, 240.2, 252.3, 320.1, 69.4

[56] References Cited

U.S. PATENT DOCUMENTS

| | | | |
|---|---|---|---|
| 4,689,402 | 8/1987 | Sekine et al. | 530/399 |
| 4,849,359 | 7/1989 | Sekine et al. | 435/252.33 |

OTHER PUBLICATIONS

Chen, T. et al., *Transgenic Models in Medicine and Agriculture: Symposium*, Wiley-Liss, New York, pp. 127–139, 1990.
Perez-Sanchez, J. et al., *J. Exp. Zool.*, 262 (3): 287–290, 1992.
Foucher, J. L. et al., *J. Steroid Biochem. Mol. Biol.*, 39(6): 975–986, 1991.
Dugvay, S. J. et al., *Molecular Endocrinology*, 6(8): 1202–1210, Sep. 1992.
Cao, Q.-P., et al., *Molecular Endocrinology*, 3(12): 2005–2010, 1989.
Shamblott, M. J. et al., *PNAS*, 89(19): 8913[00e2]14 17, Oct. 1992.
Kelley, K. M. et al., *J. Exp. Zool.*, 263(2): 220–224, 1992.
Skyrud, T. et al., *Gen. Comp. Endocrinol.*, 75(2): 247–55, 1989.
Newsted, J. L. et al., *Gen. Comp.. Endocrinol.*, 83(3): 345–53, 1991.
Zhang, P. et al., *Mol. Reprod. Dev.*, 25(1): 3–13, 1990.
Foucher, J. L. et al., *Gen. Comp. Endocrinol.*, 85(1):101–110, 1992.
McCormick, S. D. et al., *Gen. Comp. Endocrinol.*, 86(3): 398–406, 1992.
Froesch et al, 1985, *Ann. Rev. Physiol.*, vol. 47, pp. 443–467.
Funkenstein et al, 1989, Growth Hormone Increases Plasma Levels of Insulin–like Growth factor (IGF–1) . . . , *Journal of Endocrinology*, vol. 120, pp. R19–R21.
Bautista et al, 1990, Insulin–like Growth Factors I and II are Present in the Skeletal Tissues of Ten Vertebrates, *Metabolism*, vol. 39, pp. 96–100.
McCormick et al, 1991, Osmoregulatory Actions of Insulin–like Growth Factor–I in Rainbow Trout (*Oncorhynchus mykiss*), *Journal of Endocrinology*, vol. 130, pp. 87–92.
Reinecke et al, 1992, Peptides Related to Insulin–like Growth Factor 1 in . . . Bony and Cartilaginous Fish, *Regulatory Peptides*, vol. 37, pp. 155–165.
Daughaday et al, 1985, Insulin–like Growth Factors I and II of Nonmammalian Sera, *General and Comparative Endocrinology*, vol. 59, pp. 316–325.

*Primary Examiner*—Marianne P. Allen
*Attorney, Agent, or Firm*—Burns, Doane, Swecker & Mathis

[57] ABSTRACT

DNA sequences encoding rainbow trout IGF-I and IGF-II, vectors for the expression of these sequences, and cells transformed with vectors containing these sequences are disclosed. Also disclosed are the recombinant protein and peptides produced from these sequences, antibodies and kits for the detection of IGF-I and IGF-II in fish, and methods for stimulating growth of fish using rainbow trout IGF-I and IGF-II recombinant protein or vectors encoding these proteins.

4 Claims, 6 Drawing Sheets

FIG. 1

MULTIPLE 3' FORMS OF RAINBOW TROUT LIVER IGF I

```
                 5"
                   1                                                          50
     Tc2-121-6  TAAATCCGTC  TCCAGTTCGC  TAAATCTCAC  TTCTCAAAAA  CGAGCCTGCG
     Tc2-061-6  ----------  ---T------  ----------  -----C----  ----------
      Igfi4-10  ..........  ..........  ..........  ..........  ..........
      Igfil-4   ..........  ..........  ..........  ..........  ..........
                  51                                                         100
         IGFIa  CAATGGAACA  AAGTCGGAAT  ATTGAGATGT  GACATTGCCT  GCATCTTATC
         IGFIb  ----------  ----------  ----------  ----------  ----------
         IGFIc  ..........  ..........  ..........  ..........  ..........
         IGFId  ..........  ..........  ..........  ..........  ..........
                 101                                                         150
            a  CACTTTCTCA  CTGTTTTTAA  TGACTTCAAA  CAAGTTCATT  TTTGCTGGGC
            b  ----------  ----------  ----------  ----------  ----------
            c  ..........  ..........  ..........  ..........  ..........
            d  ..........  ..........  ..........  ..........  ..........
                 151                                                         200
            a  TTTGTCGTGC  GGAGACCCGT  GGGGATGTCT  AGCGGTCATT  TCTTCCAGTG
            b  ----------  ----------  ----------  ----------  ----------
            c  ..........  ..........  ..........  ..........  ..........
            d  ..........  ..........  ..........  ..........  ..........
                 201                                                         250
            a  GCATTTATGT  GATGTCTTCA  AGAGTGCGAT  GTGCTGTGTC  TCCTGTACCC
            b  ----------  ----------  ----------  ----------  ----------
            c  ..........  ..........  ..........  ..........  ..........
            d  ..........  ..........  ..........  ..........  ..........
                 251                                                         250
            a  ACACCCTCTC  ACTGCTGCTG  TGCGTCCTAA  CCCTGACTTC  GGCGGCAACA
            b  ----------  ----------  ----------  ----------  ----------
            c  ..........  ..........  ..........  ..........  ..........
            d  ..........  ..........  ..........  ..........  ..........
                 301                                                         350
            a  GGGGCGGGGC  CCGAGACCCT  GTGTGGGGCG  GAGCTGGTGG  ACACGCTGCA
            b  ----------  ----------  ----------  ----------  ----------
            c  ..........  ..........  ..........  ..........  ..........
            d  ..........  ..........  ..........  ..........  ..........
                 351                                                         400
            a  GTTTGTGTGT  GGAGAGAGAG  GCTTTTATTT  CAGTAAACCA  ACGGGGTATG
            b  ----------  ----------  -A--------  ----------  ------C---
            c  ..........  ..........  ..........  ..........  ..........
            d  ..........  ..........  ..........  ..........  ..........
                                                                             3'
```

--- : identity with a (IGF Ia)
... : gap
ACG: sequence from cDNA library
acg: sequence from PCR

```
5'    401          IGF IC                    A REGION        450
   a  GCCCCAGTTC  ACGGCGGTCA  CATAACCGTG  GTATTGTGGA  CGAGTGCTGC
   b  ----------  ----------  ----------  ----------  ----------
   c  ..........  ----------  ----------  ----------  ----------
   d  ..........  ----------  ----------  ----------  ----------

451                                              | D 500
   a  TTCCAGAGTT  GCGAGCTACG  GCGGCTCGAA  ATGTACTGTG  CCCCTGTCAA
   b  ----------  -------GA-  ----------  ----------  ----------
   c  ----------  -------ga-  ----------  ----------  ----------
   d  ----------  -------ga-  ----------  ----------  ----------

501  REGION  |           E REGION                   550
   a  GTCTGGCAAG  GCAGCTCGCT  CTGTGCGCGC  ACAGCGCCAC  ACAGACATGC
   b  ----------  ----------  -A--------  ----------  ----------
   c  ----------  ----------  -a--------  ----------  ----------
   d  ----------  ----------  -a--------  ----------  ----------

551                                                  600
   a  CAAGAACACC  TAAGGTTAGT  ACTGCAGTGC  AAAGCGTGGA  CAGAGGCACA
   b  ----------  ----AAACC-  TTAT-T-G--  -T-----...  ..........
   c  ----------  ..........  ----------  ----------  ..........
   d  ----------  ----------  ----------  --a-------  ----------

601                                                  650
   a  GAGCGTAGGA  CAGCACAGCA  CCCAGACAAG  ACAAAACCCA  AG........
   b  ..........  ..........  ..........  ..........  ..........
   c  ..........  ..........  ..........  ..........  ..........
   d  ----------  ----------  ----------  ------a---  --aagaaacc 651                                                  700
   a  ..........  ..........  ........AA  GGAGGTACAT  CAGAAGAACT
   b  ..........  .....TCACC  CATCTTGC--  ----------  ----------
   c  ..........  ..........  ..........  ----------  ----------
   d  tttatctggg  catagtcacc  catcttgc--  ----------  ----------

701                                        *        750
   a  CAAGTCGAGG  AAACACAGGG  GGAAGGAACT  ACCGAATGTA  GAAGAAGACA
   b  ----------  ----------  -----A----  ---------.  ..........
   c  ----------  ----------  -----a----  ---------.  ...-a-----
   d  ----------  ----------  -----a----  ---------.  ...-a-----
                                                             *

751                                                  800
   a  GAAGCTAACG  GACAGGCAGA  CAGGGATGAG  AGAAGGGTGG  GCCCATACCT
   b  ----------  -------G--  --C-------  ----------  ----------
   c  ----------  -------g--  --c-------  ----------  ----------
   d  ----------  -------g--  --c-------  ----------  ----t-----

801                                                  850
   a  GGTGCCTCTG  TGGAATGGTT  CACTGTAAAA  CAACAAAAGG  TGGATTATGG
   b  ------C---  --------C-  ----------  ----------  ------A---
   c  ------c---  --------c-  ----------  ----------  ------a---
   d  ------c---  --------c-  ----------  ----------  ------a---

851              121-7INT-1
   a  TACTAAGCTA  ATGGTAATAA  GCTTTGTGTG  TA
   b  ---A-T----  ----------  ----------  --
   c  ---a-t----  ----------  ----------  --
   d  ---a-t----  ----------  ----------  --
                                                3'
``` a    MSSGHFFQWHLCDVFKSAMCCVSCTHTLSLLLCVLTLTSAATGAGPETLCGAELVDTLQFVCGERGFYFSKPTGYGPSSRRSHNRGIVDECCF
b         MITPTV.  .HTM.SS.LFY.A..L..F..S.......A.....D....N.....S.....APQT......
c    METQKRHEYHSVCHTCRRTENTRMKVKMM.SSNRVEVIAEA... YTVEV.SA......ED......R..S..RSN....Q........E.....
d                      MGIPMGKSMLVL.TFLAFASCCIAAYRPS.......G.......D...R..AS..RV..........E.....
         |————A————|——D—|————————B————————|————————————C————————————|

QSCELRRLEMYCAPVKSGKAARSVRAQRHTDMPRTPKVSTAVQSVDRGTERRTAQHPDKTKPKKEVHQKNSSRGNTGGRNYRM*
     R..D.........L.PA.S..............K.............SLQII..M..F..IK..D..P..KHVTVKYSKYE.AWQR.AAQR.LRREV.PA.IERA..KF..RQAVKI.KAQEQ.AMF.HRPL
     R..D.NE...Q.....PA..SE..D..S.                          P      F..VLPDNFPRYPVGKFFQY..TW..KQSTQRLRRGL.PA.LERA..RGHVLAKELEAF..REAKR.HRPL
     R..D.AE..T.....TPA..SE..D..ST                                                  Q....L..A....SA..NK......
         |————A————|——D—|————————B————————|————————————C————————————|

ITEPSKLEPVLPPTDNYVSHN*
     ALPTQDEAHGAPPEMASNRK*

DNA ENCODING INSULIN-LIKE GROWTH FACTOR II ISOLATED FROM RAINBOW TROUT

BACKGROUND OF THE INVENTION

1. Field of the Invention

This invention relates to isolated DNA fragments encoding insulin-like growth factors I and II (IGF-I, IGF-II) isolated from the rainbow trout, *Oncorhynchus mykiss*, and to nucleotide probes and amplification primers specific for rainbow trout IGF-I and IGF-II, expression vectors containing the DNA encoding rainbow trout IGF-I and IGF-II, and to recombinantly produced rainbow trout IGF-I and IGF-II proteins. The invention also relates to antibodies directed to the recombinantly produced IGF-I and IGF-II proteins, and to kits for the detection of these proteins. The invention further relates to methods of treating various fish species using either recombinantly produced rainbow trout IGF-I and IGF-II proteins, or using DNA constructs containing the rainbow trout IGF-I- and IGF-II-encoding fragments.

2. Background of the Invention

The insulin gene family is an ancient and highly diverse group which includes insulin and insulin-like growth factor I (IGF-I) from a variety of species, mammalian insulin-like growth factor II (IGF-II), relaxin, insect prothoracicotrophic hormone (PTTH), and molluscan insulin-related peptide (MIP) (Blundell et al, (1980) *Nature (London)* 287, 781–787; Smit et al, (1989) *Nature (London)* 331, 535–538). IGFs are mitogenic peptide hormones that play an important role in the growth and differentiation of vertebrates (Froesh, E. R. (1983) in *Insulin-like growth factors/somatomedins*, ed. Spencer, M. (de Gruyter, New York), pp. 13–29).

Both insulin and IGFs are translated as prepropeptides, which can be divided into an $NH_2$-terminal prepeptide, a B-domain, a C-domain, and an A-domain. IGFs consist of an additional D-domain and COOH-terminal E-domain trailer peptide. The IGF prepeptide leader and trailer peptide are proteolytically removed, as is the insulin prepeptide leader. However, unlike IGF's, insulin is further processed by the removal of the internal C polypeptide domain.

IGF-I and IGF-II share approximately 50% homology. The mature form of mammalian IGF-I is a basic protein consisting of 70 amino acid residues. Two forms of IGF-I have been identified, which share approximately 95% homology. However, these two forms appear to have different biological roles. Liver, under the influence of pituitary growth hormone, is the primary site of IGF-I production. The mature form of mammalian IGF-II is a neutral protein consisting of 67 amino acid residues and is produced primarily in the liver, under the control of placental lactogen (Gray et al, (1987) *DNA* 6, 283–295) during prenatal development.

IGF-I and IGF-II are ubiquitous and essential regulators of cell division and vertebrate growth, and are thought to play a role in various stages of development. IGF-I is thought to be more significant in adult growth and development, while IGF-II has generally been considered a fetal form of IGF-I. Elevated levels of both IGF-I and IGF-II have been correlated to substantial increases in growth, including both mass and length, in a number of animal species.

IGF-I has been identified, either at the protein or nucleic acid level in a number of non-mammalian vertebrates including chicken (Dawe et al, (1988) *J. Endocrinol.* 177, 173–181), *Xenopus laevis* (Kajimoto et al, (1990) *Mol. Endocrinol.* 4, 217–225), coho salmon (Cao et al, (1989) *Mol. Endocrinology* 3, 2005–2010), and atlantic hagfish (Nagamatsu et al, (1991) *J. Biol. Chem.* 226, 2397–2404). IGF-I isolated from coho salmon and mammalian IGF-I share only an 80% homology at the amino acid level. IGF-II has not been identified in a fish species prior to the present invention, nor have the mRNA levels of IGF-I or II been determined in any fish species.

To date, there has been no efficient method for treating fish with recombinantly produced IGFs, or for effecting elevated levels of IGFs in fish species using DNA constructs containing IGF genes isolated from fish. Such treatment would allow for enhanced growth of fish, which would be highly useful in the aquaculture industry.

Therefore, in view of the lack of effective methods for treating fish with IGFs to enhance growth characteristics, it should be apparent that there still exists a need in the art for such methods.

SUMMARY OF THE INVENTION

Accordingly, a major object of the present invention is to provide the DNA sequences of rainbow trout IGF-I and IGF-II. Another object of the invention is to provide DNA sequences which may be used as probes or amplification primers of IGF-I and IGF-II from rainbow trout or other fish species.

A further object of the invention is to provide a DNA expression vector containing the DNA sequence for rainbow trout IGF-I and IGF-II, and cells transformed with that vector.

A still further object of the invention is to provide recombinantly produced rainbow trout IGF-I and IGF-II, antibodies directed to the recombinantly produced proteins, kits for detecting the recombinantly produced proteins, and kits for detecting the level of IGF-I and IGF-II in fish species.

Another object of the invention is to provide a DNA construct which may be used to produce transgenic fish which express rainbow trout IGF-I and IGF-II, and to provide the transgenic fish so produced.

A further object of the invention is to provide methods for enhancing the growth of fish, by either treating fish with recombinantly produced rainbow trout IGF-I and IGF-II, or by producing transgenic fish which express rainbow trout IGF-I and IGF-II.

In a first aspect, the present invention features DNA fragments encoding IGF-I and IGF-II isolated from rainbow trout. Specifically, this fragment is represented by the following nucleotide sequence for IGF-I (SEQ ID NO 1):

| | | | |
|---|---|---|---|
| 5'TCAAAAACGA | GCCTGCGCAA | TGGAACAAAG | TCGGAATATT |
| GAGATGTGAC | ATTGCCTGCA | TCTTATCCAC | TTTCTCACTG |
| TTTTTAATGA | CTTCAAACAA | GTTCATTTTT | GCTGGGCTTT |
| GTCGTGCGGA | GACCCGTGGG | GATGTCTAGC | GGTCATTTCT |

-continued

| | | | |
|---|---|---|---|
| TCCAGTGGCA | TTTATGTGAT | GTCTTCAAGA | GTGCGATGTG |
| CTGTGTCTCC | TGTACCCACA | CCCTCTCACT | GCTGCTGTGC |
| GTCCTAACCC | TGACTTCGGC | GGCAACAGGG | GCGGGGCCCG |
| AGACCCTGTG | TGGGGCGGAG | CTGGTGGACA | CGCTGCAGTT |
| TGTGTGTGGA | GAGAGAGGCT | TTTATTTCAG | TAAACCAACG |
| GGGTATGGCC | CCAGTTCACG | GCGGTCACAT | AACCGTGGTA |
| TTGTGGACGA | GTGCTGCTTC | CAGAGTTGCG | AGCTACGGCG |
| GCTCGAAATG | TACTGTGCCC | CTGTCAAGTC | TGGCAAGGCA |
| GCTCGCTCTG | TGCGCGCACA | GCGCCACACA | GACATGCCAA |
| GAACACCTAA | GGTTAGTACT | GCAGTGCAAA | GCGTGGACAG |
| AGGCACAGAG | CGTAGGACAG | CACAGCACCC | AGACAAGACA |
| AAACCCAAGA | AGGAGGTACA | TCAGAAGAAC | TCAAGTCGAG |
| GAAACACAGG | GGGAAGGAAC | TACCGAATGT | AGAAGAAGAC |
| AGAAGCTAAC | GGACAGGCAG | ACAGGGATGA | GAGAAGGGTG |
| GGCCCATACC | TGGTGCCTCT | GTGGAATGGT | TCACTGTAAA |
| ACAACAAAAG 3' | | | | and the following sequence for IGF-II (SEQ ID NO 2):

| | | | |
|---|---|---|---|
| 5" CTCTATAGCC | CTCACCAACT | GGGAAACTAA | CTCAACTGCA |
| ACCTCTCCAA | CCAAATAACG | CTCAACGTTA | GATTACTGCC |
| AATTGACATG | GAAACCCAGA | AAAGACACGA | ATACCACTCA |
| GTTTGTCACA | CCTGCCGGAG | AACGGAAAAC | ACAAGAATGA |
| AGGTCAAGAT | GATGTCTTCG | TCAAATCGAG | TGCTGGTCAT |
| TGCGCTGGCA | CTTACTCTGT | ACATTGTTGA | AGTGGCTTCG |
| GCAGAAACGC | TATGTGGAGG | AGAACTGGTG | GACGCGCTGC |
| AGTTCGTCTG | TGAAGATAGA | GGATTCTATT | TCAGTAGGCC |
| AACCAGCAGG | TCTAACAGCA | GACGCTCCCA | GAACCGTGGT |
| ATCGTGGAGG | AGTGTTGTTT | CCGTAGCTGT | GACCTCAACC |
| TGTTGGAGCA | GTACTGTGCC | AAACCTGCCA | AGTCAGAGAG |
| GGACGTGTCG | GCCACCTCTC | TACAGATCAT | TCCCATGGTG |
| CCCACAATCA | AACAGGATGT | CCCAAGAAAA | CATGTGACTG |
| TGAAGTATTC | CAAATATGAG | GCGTGGCAGA | GGAAGGCTGC |
| TCAGCGGCTC | CGGAGGGGCG | TCCCGGCCAT | CCTCAGGGCC |
| CGGAAGTTCC | GGAGGCAGGC | GGTGAAGATC | AAGCCCAAGA |
| GCAGGCGATG | TTCCACCGGC | CTCTGATCAC | CCTGCCCAGC |
| AAGCTTCCCC | CAGTCCTGCC | CCCCACGGAC | AACTACGTCA |
| GCCACAATTG | A 3' | | |

The invention also relates to fragments of this sequence which will encode biologically active fragments of rainbow trout IGF-I and IGF-II, and those which may be used as probes or DNA amplification primers which specifically bind to rainbow trout IGF-I. Also contemplated by the present invention are DNA sequences which represent modified rainbow trout IGF-I and IGF-II sequences, which differ slightly in nucleotide sequence, but still encode biologically active proteins.

In a second aspect, the present invention relates to methods of enhancing the growth of fish, by either treating fish with an amount of the IGF-I or IGF-II described above which is effective to increase the growth characteristics of those fish, or by producing transgenic fish which express the IGF-I or IGF-II described above.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1 is the nucleotide alignment of trout IGF-I [SEQ ID NO: 1] and IGF-II [SEQ ID NO: 2].

DETAILED DESCRIPTION OF THE PREFERRED EMBODIMENTS OF THE INVENTION

One may use any method known in the art for isolation of the DNA sequence of rainbow trout IGF-I and IGF-II (rtIGF-I, rtIGF-II). Such methods include genomic DNA cloning, PCR-based cloning, and cDNA cloning. For the present invention, cDNA cloning is preferable.

As a source of mRNA for the cDNA cloning strategy, one may use any tissue isolated from rainbow trout which expresses rtIGF-I and II mRNA, but liver is especially useful due to the high expression levels present there. Tissue is minced and total RNA extracted from the tissue using methods well known in the art. PolyA$^+$ mRNA is then isolated by known methods using affinity chromatography on oligo(dT)-cellulose, and the complementary DNA is produced from the mRNA using reverse transcriptase.

The cDNA so produced is then ligated into any DNA vector which can be replicated and used to transform cells for screening for the genes of interest. Such vectors include plasmid vectors and bacteriophage vectors. The bacteriophage vector λ ZAP II (Stratagene, La Jolla, Calif.) is especially useful for the present invention. The cDNA is treated so that it has either blunt ends, or ends which are compatible with a particular restriction site in the vector, and is ligated into the vector. In the case of phage vectors, the DNA must be packaged and amplified using known methods such as the plate lysate method. For plasmid vectors, the DNA is transformed into cells, the cells are grown, and DNA is isolated using known methods.

Cells containing the vector with the DNA insert are plated and grown on agar plates with selective medium, and are lifted onto membranes, which include those made of nitrocellulose or nylon, for screening with probes specific to rtIGF-I or II. The membranes are treated by methods well known in the art to lyse the cells and prepare them for hybridization to probes.

Any probe which will bind specifically to rtIGF-I or II may be used. Preferable probes are in the range of 100 to 2000 nucleotides, more preferably 100 to 1000 nucleotides, and most preferably 250 to 750 nucleotides long. The probes are labelled by any method known in the art, such as nick translation, random priming, and end labelling. Any detectable marker may be used for labelling, but radioactive nuclides are especially suitable for the present invention. Approximately $1 \times 10^5$ to $1 \times 10^6$ CPM/ml are added to the membranes in a suitable hybridization mixture, and the probes are allowed to hybridize 24 to 48 hours at 60° to 75° C. The membranes are then washed to remove excess probe, and exposed to autoradiographic film to identify positive clones.

Inserts from positive clones are then subcloned into a suitable sequencing vector, such as pBS or M13mp18 or 19 (Stratagene, La Jolla, Calif.). Sequencing may be done by any method known in the art, but dideoxynucleotide chain termination is preferable. Sequences can then be compared to other known IGF sequences using alignment programs which are well known in the art. Alternatively, sequences may be compared using PCR amplification and by Southern blot analysis. Fragments of the DNA encoding rtIGF-I and II may then be used as probes or PCR primers for IGF-I and II in any fish species.

Protein may be generated from clones containing the rtIGF-I and II sequences, by cloning the coding regions of rtIGF-I and II into an expression vector. Any expression vector may be used for expression in prokaryotes such as E. coli, or eukaryotes, such as yeast or insect cells. In addition, protein may be generated from a rainbow trout hepatoma cell line, RTH149, which naturally produces IGF-I and IGF-II, or which could be transformed with an expression plasmid containing the rtIGF-I or II sequences, to produce additional rtIGF-I and II. Protein may be isolated and purified from these cells by any method, and that protein, or peptides thereof, can then be used to generate polyclonal or monoclonal antibodies. These antibodies may be used to monitor levels of IGF-I and II in other fish species, including other finfish and shellfish, such as shrimp, in order to monitor the effectiveness of fish food, and to monitor growth characteristics of the fish.

Kits including the anti-IGF antibodies may be produced to detect the levels of IGF-I and IGF-II in fish. Such kits may contain at least one antibody which binds to IGF-I or IGF-II, a diluent, and a specific label which allows for the detection of the antibody-IGF complex. The antibody may be directly labelled with any detectable marker known in the art, including radioactive nuclides, fluorescent markers, enzymatic markers and the like. Alternatively, a second antibody may be included in the kit, which is labelled, and which binds to the anti-IGF antibody.

Protein or biologically active peptides generated by cleavage of the protein, or by expression of a portion of the protein, may be used as food supplements for any fish species, including rainbow trout, other finfish and shellfish, such as shrimp. Alternatively, fish may be treated with DNA vectors carrying the genes encoding rtIGF-I and II, so that they express higher levels of these proteins. Specifically, transgenic fish may be generated which express elevated IGF levels, leading to enhanced growth characteristics.

The following examples are presented in order to more fully illustrate the preferred embodiments of the invention. They should in no way be construed, however, as limiting the broad scope of the invention.

EXAMPLE 1

Synthesis of eDNA and Library Construction

A liver was carefully dissected from a rapidly growing juvenile rainbow trout and frozen in liquid nitrogen. Total RNA was isolated using the modified phenol-chloroform-NaDodSO$_4$ method (Agellon et al, (1986) *Canadian Journal of Fisheries and Aquatic Sciences (Canada)* 43, 1327–1331). Affinity chromatography on oligo(dT)-cellulose was carried out to enrich for poly(A)$^+$ RNA as described (Aviv et al, (1972) *Proc. Natl. Acad. Sci. USA* 69, 1408–1412). Double stranded cDNA (dscDNA) was generated from approximately 5 μg of poly(A)$^+$ enriched RNA using a commercially available (Pharmacia, Piscataway, N.J.) modified Gubler-Hoffman cDNA synthesis method (Gubler (1983) *Gene* 25, 263"269). Of the approximately 2.4 μg dscDNA generated, 60 ng was ligated into the EcoRI restriction enzyme recognition site of the bacteriophage vector λ ZAP II (Stratagene, La Jolla, Calif.). After in vitro packaging, approximately one million recombinant phage were generated and amplified by the plate lysate method.

EXAMPLE 2

Screening of cDNA library and Radioactive Probe labeling

Approximately one million recombinant bacteriophage from the trout liver cDNA library were plated, lifted in duplicate onto nylon membranes (Msi, Westhoro, Mass.) and incubated overnight at 65° C. in a hybridization solution (0.6M NaCl, 0.02M EDTA pH 8.0, 0.2M Tris pH 8.0, 0.5% NaDodSO$_4$, 0.1% Sodium pyrophosphate) containing $1 \times 10^6$ CPM/ml of double-stranded DNA probe radiolabeled using the random hexamer priming method (Feinberg et al, (1983) *Anal. Biochem.* 132, 6–13). In vivo excision of λ ZAP II phage to a plasmid was used to facilitate recombinant DNA preparation and characterization. Oligonucleotides used in later characterization of cDNA clones were end-labeled with $\gamma^{32}$P-dATP using a standard polynucleotide kinase method (Maniatis et al, (1982) in *Molecular Cloning: A Laboratory Manual* (Cold Spring Harbor Laboratory Press, Cold Spring Harbor, N.Y.) pp. 111).

In order to isolate cDNA coding for trout insulin family members, including IGFs, a strategy was employed that capitalized on the areas of strong nucleotide conservation which define the family. A multiple sequence nucleotide alignment was carried out manually on insulin gene family members. Included in this alignment were insulin of anglerfish (Hobart et al, (1980) *Science* 210, 1360–1363), coho salmon (Sorokin et al, (1982) *Gene* 20, 367–376), carp (Hahn et al, (1983) *Nuc. Acid. Res.* 11, 4541–4552), and hagfish (Chan et al, (1981) in *Biol. chem.* 256, 7595–7602), rat IGF-I (Casella et al, (1987) *DNA* 6, 325–330), human IGF-II (Shen et al, (1988) Proc. *Natl. Acad. Sci. USA* 85, 1947–1951), and molluscan insulin-related peptide. Two oligonucleotides were designed as 20-mers with 32 degenerate forms, and oriented so that the polymerase chain reaction could be carried out to amplify the region between them. These oligonucleotides had the following sequences: (SEQ ID NO. 3) A20:

5' C A G/A C A C T C/G C/A T C C/A A C G/A A T G C C 3'

(SEQ ID NO. 4) B20:

5' G A G/C C T G G T G G A C G/A C C/T C T C/T C/T A 3'

Approximately 100 ng of trout liver dscDNA was used as a PCR template. The PCR was carried out under the following standard conditions: 95° C. denaturation, 42° C. primer annealing, and 72° C polymerization for 30 cycles. Upon resolution of the PCR product, a band of the predicted size (120 base pairs) was evident. This fragment was cloned and its nucleotide sequence determined. The resultant nucleotide sequence had an approximately 97% identity to the corresponding region of the cDNA sequence of coho salmon IGF-I. The PCR fragment, designated as IGF-P, was used as a probe to isolate the full length cDNA clones of trout IGF. Oligonucleotides A20 and B20 were also used to amplify IGF-I and II from other fish species including eel, seabream, dogfish and lamprey.

Screening of the trout liver cDNA library with IGF-P resulted in the identification of 38 positive clones, 12 of which were chosen for further plaque purification.

EXAMPLE 3

DNA sequencing and analysis

Inserts of cDNA clones were subcloned into the replicative form I of M13mp1S. Nucleotide sequences of the cDNA inserts were determined in both directions by the dideoxynucleotide chain-termination method (Sanger et al, (1977) *Proc. Natl. Acad. Sci. USA* 74, 5463–5467). Comparisons of nucleic acid and predicted amino acid sequences between two IGFs were made using the GAP (Genetics Computer Group, Madison, Wis.) alignment program which uses the algorithm of Needleman and Wunsch (Needleman & Wunsch, (1970) *J. Mol. Biol.* 48, 443–453). Gap weight values (gap weight reflects the number of positive matches the program must accrue to justify the addition of one gap) of 5.0 and 3.0 were used for nucleotide and predicted amino acid comparisons, respectively. Gap length weight values (an additional criterion for gap introduction calculated as gap length weight×gap length) of 0.30 and 0.10 were used for nucleotide and predicted amino acid comparisons, respectively. Predicted amino acid similarity is a measure of relatedness based on the evolutionary distance between amino acid residues as normalized by Gribskov and Burgess (Gribskov & Burgess (1986) *Nuc. Acid. Res.* 14, 6745–6763). Similarity was scored when the similarity threshold between two predicted amino acid residues was greater than or equal to 0.50. Predicted amino acid multiple sequence alignments were made using PILEUP (Genetics Computer Group, Madison, Wis.). Values of gap weight and gap length weight used in PILEUP were identical to those used in the GAP program. Coho salmon and human IGF sequences were accessed through the GenBank (release 69.0, 9/91) Database.

At the nucleotide level, two of the trout cDNA clones which were saIGFC probe positive were 100% identical to each other except in the length of the 5' untranslated region. These clones were identified as rtIGF-I based on a 98.7% nucleotide identity to salmon IGF-I over the entire coding region. At the predicted amino acid level, only 3 of 176 residues differ (98.3% identity and 99.4% similarity) between rtIGF-I and salmon IGF-I. The putative mature protein forms of these two molecules have identical predicted amino acid sequence. Two of the trout cDNA clones which failed to hybridize to the saIGFC probe, were 100% identical to each other except in the length of the 5' untranslated regions and had a 46.1% nucleotide identity over the entire coding region, as well as a 43.3% identity and 61.0% similarity at the predicted amino acid level to rtIGF-I. These cDNA clones were identified as rtIGF-II. The nucleotide and predicted amino acid sequences of rtIGF-I and II presented in FIG. 1 illustrate the differences between these two molecules.

FIG. 1 shows the nucleotide alignment of two trout IGF cDNAs. The identity of each sequence is as follows: (a), trout IGF I; (b), trout IGF II. Identity between (a) and (b) is indicated by "1". Predicted amino acid sequences are indicated in uppercase one letter code above the first nucleotide of each codon in (a), and below the first nucleotide of the codon in (b). Amino acid differences with coho salmon IGF I are indicated in lowercase one letter code above sequence (b). The stop codon is indicated as "*" above and below (a) and (b) respectively. Algorithmically introduced gaps in the nucleotide sequences are indicated as ".". The beginning of IGF B-, C-, A-D-, and E-domains are indicated in uppercase above (a) and below (b).

Figure 2:
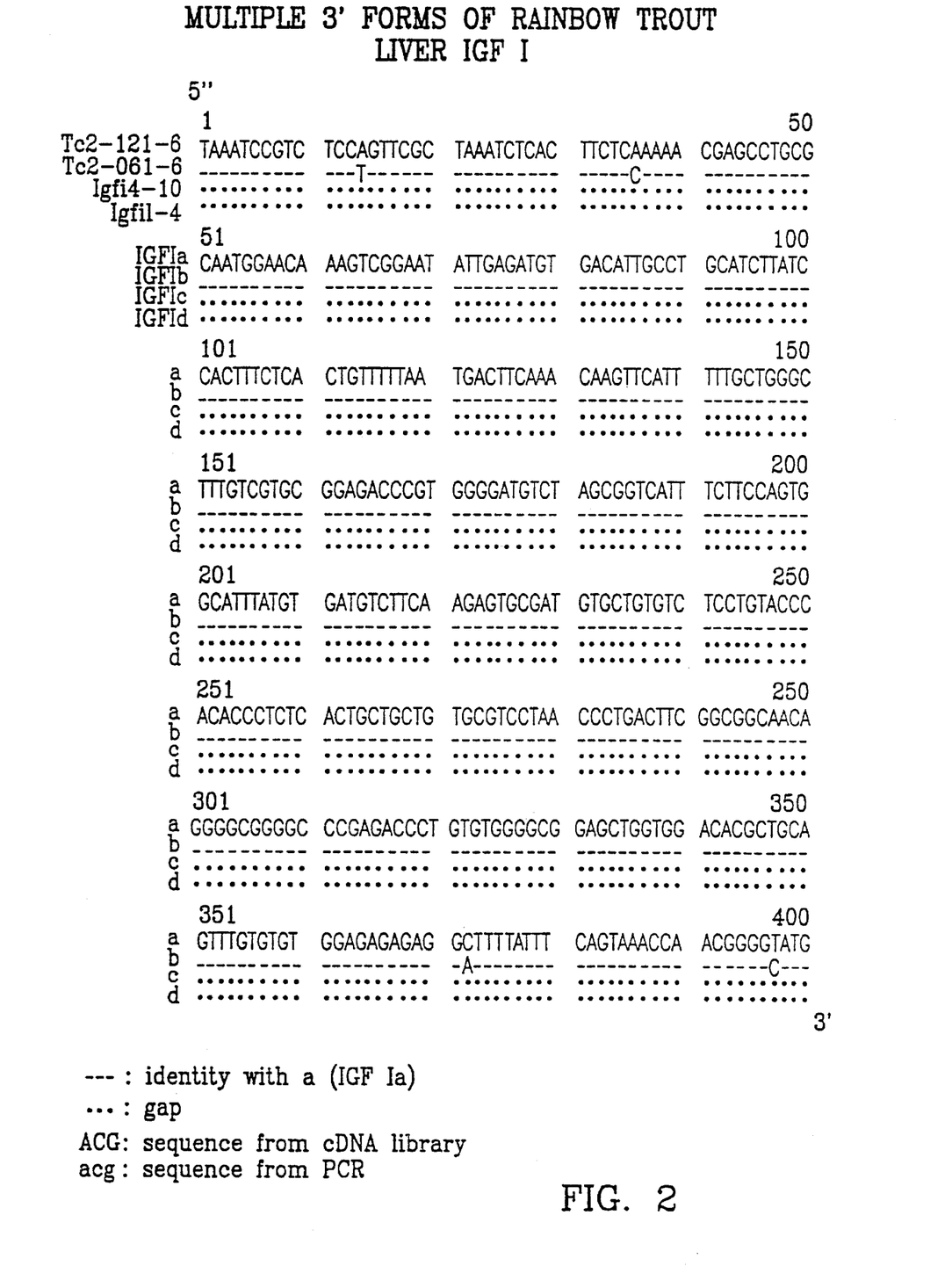
FIG. 2 is the nucleotide sequences of multiple forms of rainbow trout liver IGF-I which appear to be distributed differently depending on developmental states and tissue [SEQ ID NOS.: 5–8].

In addition, multiple forms of IGF-I have been identified, which appear to be distributed differently depending on developmental stage, and tissue type. (FIG. 2).

EXAMPLE 4

Relationship to human IGF I and II

When human IGF-I (Tobin et al, (1990) *Mol. Endocrinol.* 4, 1914–1920) and II (Irminger et al, (1987) *Proc. Natl. Acad. Sci. USA* 84, 6630–6634) were compared at the nucleotide and predicted amino acid levels, 46.3% and 43.5% identity respectively, as well as a 58.1% predicted amino acid similarity resulted. In order to compare the relationships shared by rtIGF-I and II with those of human IGF-I and II, a multi-sequence alignment was done at the predicted amino acid level (FIG. 3).

Figure 3:
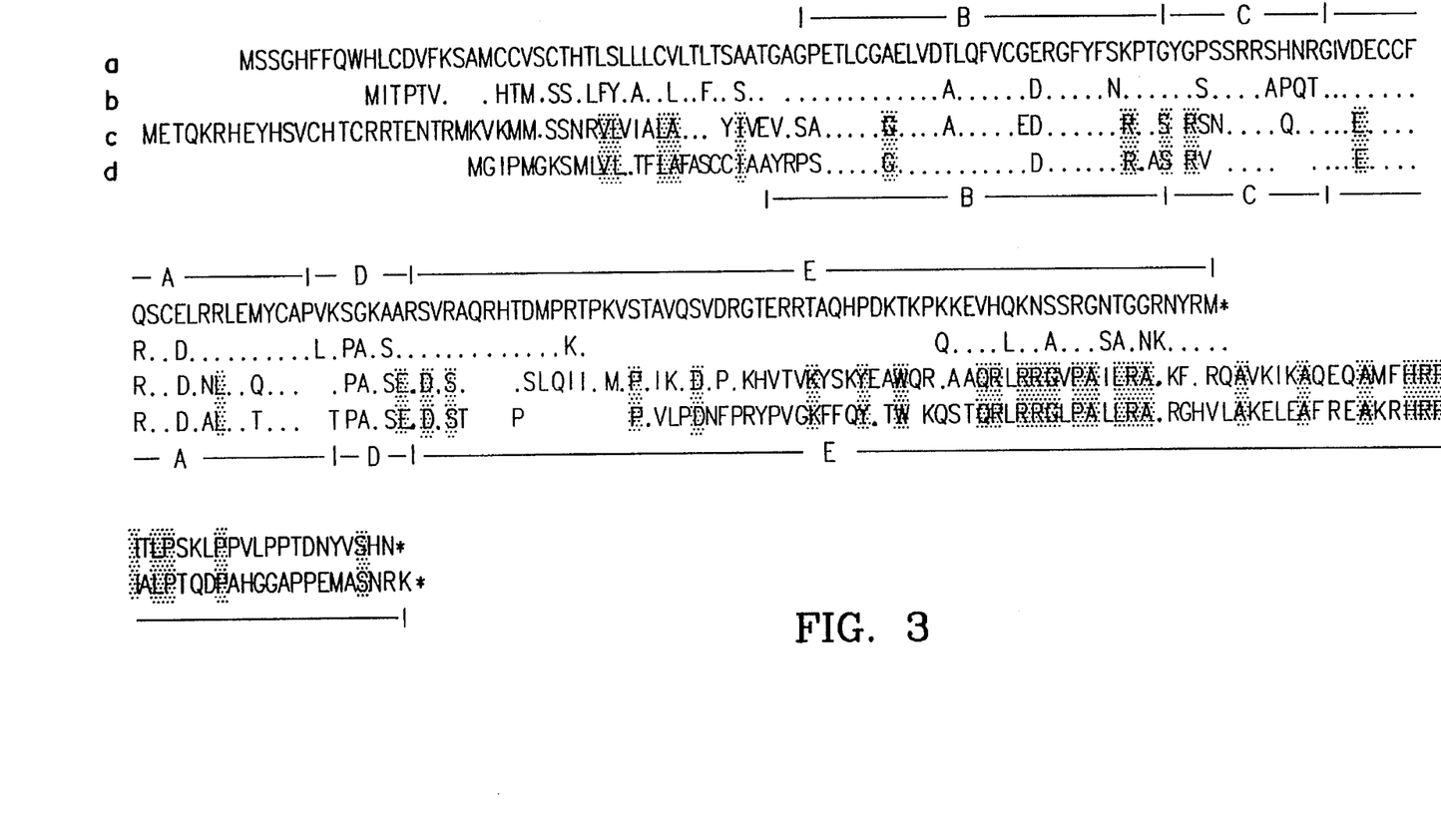
FIG. 3 is the multiple predicted amino acid level alignment of trout and human IGFs [SEQ ID NOS.: 9–12].

FIG. 3 shows the multiple predicted amino acid level alignment of trout and human IGFs. The identity of each sequence is as follows: (a) trout IGF I; (b) human 0 IGF I; (c) trout IGF II; (d) human IGF II. Predicted amino acids are indicated in uppercase one letter code. The stop codon is indicated as "*". Identity with (a) is indicated as ".". Identity only between (c) and (d) is indicated by shading. Algorithmically introduced gaps are indicated by the absence of one letter code. The putative IGF domain boundaries are indicated in bold above (a) for IGF I and below (d) for IGF II.

This multiple alignment indicates strong predicted amino acid conservation between all four IGFs in the B- and A-domains and in the six cysteine residues present in the putative mature protein form (based on analogy to human IGF I and II domain boundaries). Cysteine residues not present in the mature protein are not conserved, however.

The multiple alignment also indicates 41 residues conserved only between IGFs (shading in FIG. 3). Although some of these identities are likely to be fortuitous, some may represent areas with particular functional significance. In this respect, it is interesting to note that most of the IGF-II-specific identities (29 of 41) are located in the E-domain, a region for which biological relevance has not yet been ascribed.

To quantify the relationships indicated in FIG. 3, IGFs were compared to each other individually. In this analysis, rtIGF-I was found to be most similar to human IGF-I (70.8% identity and 79.6% similarity with human IGF I, 39.8% identity and 54.9% similarity with human IGF-II) and rtIGF-II was found to be most similar to human IGF-II (53.6% identity and 64.8% similarity with human IGF-II, 48.1% identity and 60.7% similarity with human IGF-I). Additionally, rtIGF-I was more similar to rtIGF-II (43.3% identity and 60.9% similarity) than human IGF-II (39.8% identity and 54.9% similarity). The predicted sizes of mature rtIGF protein forms are close to those of human IGFs. Both rtIGFs and human IGF-I are 70 residues in length, while human IGF-II is 67 residues.

EXAMPLE 5

Reverse transcriptase/Polymerase Chain Reaction (PCR) Assay

Single-stranded cDNA (sscDNA) was generated from trout liver RNA using avian myoblastoma virus (AMV) reverse transcriptase (Boehringer, Indianapolis, Ind.) and oligo(dT) primer. A small fraction of the sscDNA was used as a PCR template. The PCR primers used were designed to amplify a region between the C- and E-domains of rtIGF-I and II.

PCR controls included approximately 1 ng of either rtIGF-I or II cDNA cloned into the Bluescript (Stratagene, La Jolla, Calif.) plasmid vector with both compatible and incompatible primers, and a reaction done in the absence of template and all 4 primers.

In order to partially standardize the PCR results, oligonucleotide primers for an approximately 800 bp internal fragment of trout β-actin were included in all PCR reactions. After 25 cycles of 95° C. denaturation, 60° C. primer annealing, and 72° C. polymerization, the PCR products were resolved on a 3% agarose gel which was bidirectionally transferred to nylon membranes. The membranes were then probed with a mixture of a radiolabeled rainbow trout β-actin PCR product probe plus either a radiolabeled rtIGF-I or II cDNA probe.

This sensitive reverse transcriptase/PCR assay was developed to detect messenger RNA (mRNA) of rtIGF-I and II in the liver of a rapidly growing juvenile rainbow trout. As indicated in FIG. 4, both rtIGF-I and II mRNAs were specifically detected, as was β-actin (compare panels A and B, lanes 1 and 2).

Figure 4:
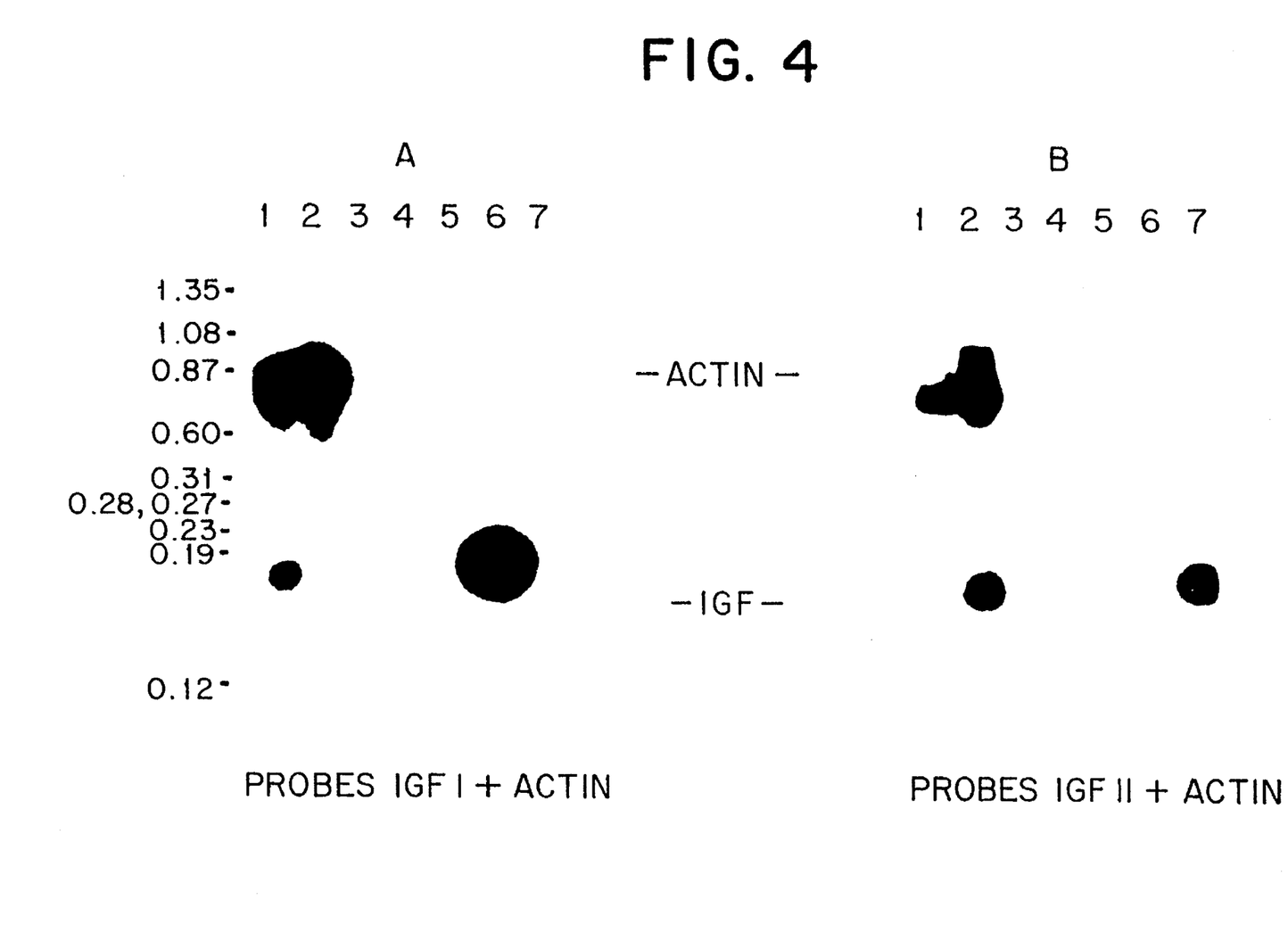
FIG. 4 is the results of a reverse transcriptase/PCR assay to detect rainbow trout IGF-I and IGF-II mRNA in the liver of rainbow trout.

FIG. 4 shows the results of a reverse transcriptase/PCR assay to detect rtIGF-I and rtIGF-II mRNA in the liver of rainbow trout. Contents of the PCR reactions are as follows: lane 1, rtIGF-I primers (IGF-I-C and IGF-I-E) and trout liver sscDNA template; lane 2, rtIGF-II primers (IGF-II-C and IGF-II-E) and trout liver sscDNA template; lane 3, both rtIGF-I and II primers, no template; lane 4, rtIGF-II primers and rtIGF-I cDNA; lane 5, rtIGF-I primers and IGF-II cDNA template; lane 6, rtIGF-I primers and rtIGF cDNA template; lane 7, rtIGF-II primers and rtIGF-II cDNA template. Probes used are indicated below panels (A) and (B) and are as follows: IGF-I, rtIGF-I cDNA; IGF-II, rtIGF-II cDNA; ACTIN, rainbow trout β-actin PCR product. Predicted sizes of the β-actin and IGF PCR products are indicated between panels (A) and (B). Size standards are the HaeIII restriction enzyme digest fragments of bacteriophage φx174 and are indicated in kilobase pairs to the left of panel (A). Evidence for the specific detection of rtIGF-I and II are indicated by hybridization of the predicted size in lane 1 of panel (A), and lane 2 of panel (B) respectively. Autoradiographic exposure times were 12 hours and 3 hours for panels (A) and (B) respectively.

This experiment indicates the presence of both IGF mRNAs in the liver of a rapidly growing juvenile rainbow trout. In addition, Northern blots of rapidly growing juvenile rainbow trout liver RNA probed with radiolabeled rtIGF-I and II indicate lower levels of rtIGF-I than II (data not shown).

EXAMPLE 6

Gemomic Southern Blot Analysis

Approximately 10 μg of rainbow trout muscle genomic DNA was digested to completion with various restriction enzymes in duplicate, resolved on an 0.8% agarose gel, and transferred to nylon membranes as described (Agellon et al, (1988) *Proc. Natl. Acad. Sci. USA* 85, 5136–5140). The Southern blots were probed with radiolabeled rtIGF-I and II cDNA. Hybridization and wash conditions were similar to those used in the cDNA library screening.

Southern blot analysis of the 12 cDNA clones suggested that more than one type of IGF was present since only 4 of the 12 cDNA clones hybridized to an end-labeled 24-mer oligonucleotide probe (saIGFC) targeted to the coho salmon IGF I C-domain.

Mammalian IGF-I and II are encoded by separate genes (Dull et al, (1984) *Nature (London)* 310, 777–781). In order to confirm that rtIGF-I and II are encoded by two separate genes, duplicate genomic Southern blots were probed with rtIGF-I and II cDNA probes (FIG. 5).

Figure 5:
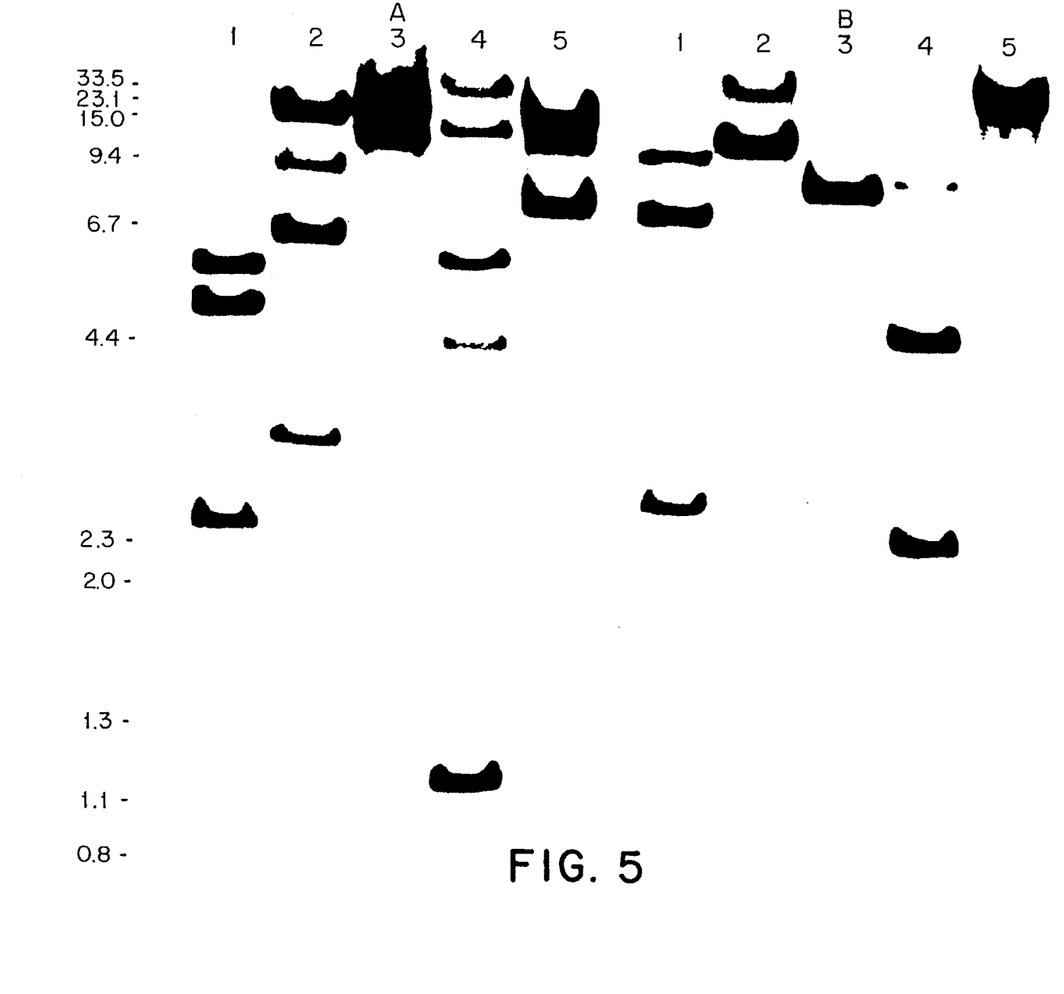
FIG. 5 is a genomic Southern blot analysis of rainbow trout IGF-I and IGF-II.

FIG. 5 shows the rainbow trout IGF genomic Southern blot analysis. Restriction enzymes used are as follows: (1) PstI; (2) XbaI; (3) BamHI; (4) HindIII; (5) EcoRI. Probes used are as follows: (A) rtIGF-I cDNA; (b) rtIGF-II cDNA. Size standard are the HindIII and XhoI restriction enzyme digest fragments of λ phage, as well as the HaeIII restriction enzyme digest fragments of bacteriophage φx174, and are indicated in kilobase pairs to the left of (A).

The absence of pattern similarity in these two blots suggests that rtIGF-I and II are encoded by two different genes. This evidence along with the widespread differences between rtIGF-I and II at the nucleotide and predicted amino acid levels suggest that the relationship between rtIGF-I and II is not analogous to that of the multiple forms of human IGF-I generated by differential RNA processing, since the latter differ only in the length and nucleotide sequence of the E-domain (Rotwein et al, (1986) *J. Biol. Chem.* 261, 4828–4832). However, the extensive conservation of nucleotide and predicted amino acid sequence in the B- and A-domains clearly identify this molecule as a member of the insulin gens family.

EXAMPLE 7

Analysis of mRNA levels of IGF-I and II in juvenile and adult rainbow trout using RNAse protection A 438 basepair region encompassing the C, A, D and E regions and a portion of the 3' untranslated region of IGF-I, and a 512 basepair region encompassing a like region of IGF-II were cloned into Bluescript (Stratagens, La Jolla, Calif.). Sense and radioactive (labelled with $^{32}$P-UTP) antisense cRNA were generated. 1×10$^5$ CPM of antisense probes approximately 100 basepairs longer than that of the cRNA were incubated with whole liver RNA from both juvenile and adult rainbow trout overnight at 50° C.. The RNA was then digested with RNAse A and RNAse T1 using standard concentrations, times and temperatures. The digestion products were then treated with Proteinass K to deactivate RNAse, precipitated and resolved on a 6% polyacrylamide gel in 8M urea. In parallel to liver RNA, 10 ng, 1 ng, 0.1 ng, 0.01 ng and 0.001 ng sense cRNA for IGF-I and II were processed. Resolution of these samples allowed for the quantitation of liver IGF-I and II mRNA levels. Results indicated that IGF-I was present at very low levels in the juvenile, and slightly higher in adults. IGF-II was present at very high levels (about 10 times the IGF-I level) in both juvenile and adult trout liver. These results suggest that IGF-II may play a more important role in growth enhancement than IGF-I.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

---

What is claimed is:

1. An isolated DNA fragment comprising a DNA sequence encoding IGF-II isolated from rainbow trout.

2. The isolated DNA fragment of claim 1 having the following sequence (SEQ ID NO 2):

| 5' CTCTATAGCC | CTCACCAACT | GGGAAACTAA | CTCAACTGCA |
| --- | --- | --- | --- |
| ACCTCTCCAA | CCAAATAACG | CTCAACGTTA | GATTACTGCC |
| AATTGACATG | GAAACCCAGA | AAAGACACGA | ATACCACTCA |
| GTTTGTCACA | CCTGCCGGAG | AACGGAAAAC | ACAAGAATGA |
| AGGTCAAGAT | GATGTCTTCG | TCAAATCGAG | TGCTGGTCAT |
| TGCGCTGGCA | CTTACTCTGT | ACATTGTTGA | AGTGGCTTCG |
| GCAGAAACGC | TATGTGGAGG | AGAACTGGTG | GACGCGCTGC |
| AGTTCGTCTG | TGAAGATAGA | GGATTCTATT | TCAGTAGGCC |
| AACCAGCAGG | TCTAACAGCA | GACGCTCCCA | GAACCGTGGT |
| ATCGTGGAGG | AGTGTTGTTT | CCGTAGCTGT | GACCTCAACC |
| TGTTGGAGCA | GTACTGTGCC | AAACCTGCCA | AGTCAGAGAG |
| GGACGTGTCG | GCCACCTCTC | TACAGATCAT | TCCCATGGTG |
| CCCACAATCA | AACAGGATGT | CCCAAGAAAA | CATGTGACTG |
| TGAAGTATTC | CAAATATGAG | GCGTGGCAGA | GGAAGGCTGC |
| TCAGCGGCTC | CGGAGGGGCG | TCCCGGCCAT | CCTCAGGGCC |
| CGGAAGTTCC | GGAGGCAGGC | GGTGAAGATC | AAGCCCAAGA |
| GCAGGCGATG | TTCCACCGGC | CTCTGATCAC | CCTGCCCAGC |
| AAGCTTCCCC | CAGTCCTGCC | CCCCACGGAC | AACTACGTCA |
| GCCACAATTG | A 3'. |

3. A DNA expression vector containing the DNA fragment of claim 1.

4. Isolated transformed host cells comprising a plasmid containing the DNA fragment of claim 1.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 770 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
TCAAAAACGA  GCCTGCGCAA  TGGAACAAAG  TCGGAATATT  GAGATGTGAC  ATTGCCTGCA      60
TCTTATCCAC  TTTCTCACTG  TTTTTAATGA  CTTCAAACAA  GTTCATTTTT  GCTGGGCTTT     120
GTCGTGCGGA  GACCCGTGGG  GATGTCTAGC  GGTCATTTCT  TCCAGTGGCA  TTTATGTGAT     180
GTCTTCAAGA  GTGCGATGTG  CTGTGTCTCC  TGTACCCACA  CCCTCTCACT  GCTGCTGTGC     240
GTCCTAACCC  TGACTTCGGC  GGCAACAGGG  GCGGGGCCCG  AGACCCTGTG  TGGGGCGGAG     300
CTGGTGGACA  CGCTGCAGTT  TGTGTGTGGA  GAGAGAGGCT  TTTATTTCAG  TAAACCAACG     360
GGGTATGGCC  CCAGTTCACG  GCGGTCACAT  AACCGTGGTA  TTGTGGACGA  GTGCTGCTTC     420
CAGAGTTGCG  AGCTACGGCG  GCTCGAAATG  TACTGTGCCC  CTGTCAAGTC  TGGCAAGGCA     480
GCTCGCTCTG  TGCGCGCACA  GCGCCACACA  GACATGCCAA  GAACACCTAA  GGTTAGTACT     540
GCAGTGCAAA  GCGTGGACAG  AGGCACAGAG  CGTAGGACAG  CACAGCACCC  AGACAAGACA     600
AAACCCAAGA  AGGAGGTACA  TCAGAAGAAC  TCAAGTCGAG  GAAACACAGG  GGGAAGGAAC     660
TACCGAATGT  AGAAGAAGAC  AGAAGCTAAC  GGACAGGCAG  ACAGGGATGA  GAGAAGGGTG     720
GGCCCATACC  TGGTGCCTCT  GTGGAATGGT  TCACTGTAAA  ACAACAAAAG                 770
```

( 2 ) INFORMATION FOR SEQ ID NO:2:

( i ) SEQUENCE CHARACTERISTICS:
        ( A ) LENGTH: 732 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| CTCTATAGCC | CTCACCAACT | GGGAAACTAA | CTCAACTGCA | ACCTCTCCAA | CCAAATAACG | 60 |
| CTCAACGTTA | GATTACTGCC | AATTGACATG | GAAACCCAGA | AAAGACACGA | ATACCACTCA | 120 |
| GTTTGTCACA | CCTGCCGGAG | AACGGAAAAC | ACAAGAATGA | AGGTCAAGAT | GATGTCTTCG | 180 |
| TCAAATCGAG | TGCTGGTCAT | TGCGCTGGCA | CTTACTCTGT | ACATTGTTGA | AGTGGCTTCG | 240 |
| GCAGAAACGC | TATGTGGAGG | AGAACTGGTG | GACGCGCTGC | AGTTCGTCTG | TGAAGATAGA | 300 |
| GGATTCTATT | TCAGTAGGCC | AACCAGCAGG | TCTAACAGCA | GACGCTCCCA | GAACCGTGGT | 360 |
| ATCGTGGAGG | AGTGTTGTTT | CCGTAGCTGT | GACCTCAACC | TGTTGGAGCA | GTACTGTGCC | 420 |
| AAACCTGCCA | AGTCAGAGAG | GGACGTGTCG | GCCACCTCTC | TACAGATCAT | TCCCATGGTG | 480 |
| CCCACAATCA | AACAGGATGT | CCCAAGAAAA | CATGTGACTG | TGAAGTATTC | CAAATATGAG | 540 |
| GCGTGGCAGA | GGAAGGCTGC | TCAGCGGCTC | CGGAGGGGCG | TCCCGGCCAT | CCTCAGGGCC | 600 |
| CGGAAGTTCC | GGAGGCAGGC | GGTGAAGATC | AAGGCCCAAG | AGCAGGCGAT | GTTCCACCGG | 660 |
| CCTCTGATCA | CCCTGCCCAG | CAAGCTTCCC | CCAGTCCTGC | CCCCACGGA | CAACTACGTC | 720 |
| AGCCACAATT | GA | | | | | 732 |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

| | | |
|---|---|---|
| CARCACTSMT | CMACRATGCC | 20 |

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

| | | |
|---|---|---|
| GASCTGGTGG | ACRCYCTYYA | 20 |

( 2 ) INFORMATION FOR SEQ ID NO:5:

( i ) SEQUENCE CHARACTERISTICS:
        ( A ) LENGTH: 846 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 642
        ( D ) OTHER INFORMATION: /note="Gap of 36 after 642."

( x i ) SEQUENCE DESCRIPTION: SEQ ID NO:5:

| | | | | | | |
|---|---|---|---|---|---|---|
| TAAATCCGTC | TCCAGTTCGC | TAAATCTCAC | TTCTCAAAAA | CGAGCCTGCG | CAATGGAACA | 60 |

```
AAGTCGGAAT ATTGAGATGT GACATTGCCT GCATCTTATC CACTTTCTCA CTGTTTTTAA      120

TGACTTCAAA CAAGTTCATT TTTGCTGGGC TTTGTCGTGC GGAGACCCGT GGGGATGTCT      180

AGCGGTCATT TCTTCCAGTG GCATTTATGT GATGTCTTCA AGAGTGCGAT GTGCTGTGTC      240

TCCTGTACCC ACACCCTCTC ACTGCTGCTG TGCGTCCTAA CCCTGACTTC GGCGGCAACA      300

GGGGCGGGGC CCGAGACCCT GTGTGGGGCG GAGCTGGTGG ACACGCTGCA GTTTGTGTGT      360

GGAGAGAGAG CTTTTATTT  CAGTAAACCA ACGGGGTATG GCCCCAGTTC ACGGCGGTCA      420

CATAACCGTG GTATTGTGGA CGAGTGCTGC TTCCAGAGTT GCGAGCTACG GCGGCTCGAA      480

ATGTACTGTG CCCCTGTCAA GTCTGGCAAG GCAGCTCGCT CTGTGCGCGC ACAGCGCCAC      540

ACAGACATGC CAAGAACACC TAAGGTTAGT ACTGCAGTGC AAAGCGTGGA CAGAGGCACA      600

GAGCGTAGGA CAGCACAGCA CCCAGACAAG ACAAAACCCA AGAAGGAGGT ACATCAGAAG      660

AACTCAAGTC GAGGAAACAC AGGGGGAAGG AACTACCGAA TGTAGAAGAA GACAGAAGCT      720

AACGGACAGG CAGACAGGGA TGAGAGAAGG GTGGGCCCAT ACCTGGTGCC TCTGTGGAAT      780

GGTTCACTGT AAAACAACAA AAGGTGGATT ATGGTACTAA GCTAATGGTA ATAAGCTTTG      840

TGTGTA                                                                846
```

( 2 ) INFORMATION FOR SEQ ID NO:6:

( i ) SEQUENCE CHARACTERISTICS:
        ( A ) LENGTH: 798 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 584
        ( D ) OTHER INFORMATION: /note="Gap of 81 after 584."

( i x ) FEATURE:
        ( A ) NAME/KEY: misc_feature
        ( B ) LOCATION: 658
        ( D ) OTHER INFORMATION: /note="Gap of 3 after 658."

( x i ) SEQUENCE DESCRIPTION: SEQ ID NO:6:

```
TAAATCCGTC TCCTGTTCGC TAAATCTCAC TTCTCCAAAA CGAGCCTGCG CAATGGAACA      60

AAGTCGGAAT ATTGAGATGT GACATTGCCT GCATCTTATC CACTTTCTCA CTGTTTTTAA      120

TGACTTCAAA CAAGTTCATT TTTGCTGGGC TTTGTCGTGC GGAGACCCGT GGGGATGTCT      180

AGCGGTCATT TCTTCCAGTG GCATTTATGT GATGTCTTCA AGAGTGCGAT GTGCTGTGTC      240

TCCTGTACCC ACACCCTCTC ACTGCTGCTG TGCGTCCTAA CCCTGACTTC GGCGGCAACA      300

GGGGCGGGGC CCGAGACCCT GTGTGGGGCG GAGCTGGTGG ACACGCTGCA GTTTGTGTGT      360

GGAGAGAGAG GATTTATTT  CAGTAAACCA ACGGGCTATG GCCCCAGTTC ACGGCGGTCA      420

CATAACCGTG GTATTGTGGA CGAGTGCTGC TTCCAGAGTT GCGAGCTGAG GCGGCTCGAA      480

ATGTACTGTG CCCCTGTCAA GTCTGGCAAG GCAGCTCGCT CAGTGCGCGC ACAGCGCCAC      540

ACAGACATGC CAAGAACACC TAAGAAACCT TTATCTGGGC ATAGTCACCC ATCTTGCAAG      600

GAGGTACATC AGAAGAACTC AAGTCGAGGA AACACAGGGG GAAGAAACTA CCGAATGTAG      660

AAGACAGAAG CTAACGGACA GGCGGACACG GATGAGAGAA GGGTGGGCCC ATACCTGGTG      720

CCCCTGTGGA ATGGTCCACT GTAAAACAAC AAAAGGTGGA TAATGGTACA ATGCTAATGG      780

TAATAAGCTT TGTGTGTA                                                   798
```

( 2 ) INFORMATION FOR SEQ ID NO:7:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 153
        ( D ) OTHER INFORMATION: /note="Gap of 117 after 153."

( i x ) FEATURE:
        ( A ) NAME/KEY: misc_feature
        ( B ) LOCATION: 214
        ( D ) OTHER INFORMATION: /note="Gap of 3 after 214."

( x i ) SEQUENCE DESCRIPTION: SEQ ID NO:7:

```
TCACGGCGGT CACATAACCG TGGTATTGTG GACGAGTGCT GCTTCCAGAG TTGCGAGCTG      60
AGGCGGCTCG AAATGTACTG TGCCCCTGTC AAGTCTGGCA AGGCAGCTCG CTCAGTGCGC     120
GCACAGCGCC ACACAGACAT GCCAAGAACA CCTAAGGAGG TACATCAGAA GAACTCAAGT     180
CGAGGAAACA CAGGGGGAAG AAACTACCGA ATGTAGAAGA CAGAAGCTAA CGGACAGGCG     240
GACACGGATG AGAGAAGGGT GGGCCCATAC CTGGTGCCCC TGTGGAATGG TCCACTGTAA     300
AACAACAAAA GGTGGATAAT GGTACAATGC TAATGGTAAT AAGCTTTGTG TGTA           354
```

( 2 ) INFORMATION FOR SEQ ID NO:8:

( i ) SEQUENCE CHARACTERISTICS:
        ( A ) LENGTH: 432 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: misc_feature
        ( B ) LOCATION: 331
        ( D ) OTHER INFORMATION: /note="Gap of 3 after 331."

( x i ) SEQUENCE DESCRIPTION: SEQ ID NO:8:

```
TCACGGCGGT CACATAACCG TGGTATTGTG GACGAGTGCT GCTTCCAGAG TTGCGAGCTG      60
AGGCGGCTCG AAATGTACTG TGCCCCTGTC AAGTCTGGCA AGGCAGCTCG CTCAGTGCGC     120
GCACAGCGCC ACACAGACAT GCCAAGAACA CCTGAGCGTA GGACAGCACA GCACCCAGAC     180
AAGACAAAAA CCAAGAAGAA ACCTTTATCT GGGCATAGTC ACCCATCTTG CAAGGAGGTA     240
CATCAGAAGA ACTCAAGTCG AGGAAACACA GGGGAAGAA ACTACCGAAT GTAGAAGACA      300
GAAGCTAACG GACAGGCGGA CACGGATGAG AGAAGGGTGG GCCCTTACCT GGTGCCCCTG     360
TGGAATGGTC CACTGTAAAA CAACAAAGG TGGATAATGG TACAATGCTA ATGGTAATAA      420
GCTTTGTGTG TA                                                         432
```

( 2 ) INFORMATION FOR SEQ ID NO:9:

( i ) SEQUENCE CHARACTERISTICS:
        ( A ) LENGTH: 176 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:9:

| Met | Ser | Ser | Gly | His | Phe | Phe | Gln | Trp | His | Leu | Cys | Asp | Val | Phe | Lys |
|---|---|---|---|---|---|---|---|---|---|---|---|---|---|---|---|
| 1 | | | | 5 | | | | | 10 | | | | | 15 | |
| Ser | Ala | Met | Cys | Cys | Val | Ser | Cys | Thr | His | Thr | Leu | Ser | Leu | Leu | Leu |
| | | | 20 | | | | 25 | | | | | 30 | | | |
| Cys | Val | Leu | Thr | Leu | Thr | Ser | Ala | Ala | Thr | Gly | Ala | Gly | Pro | Glu | Thr |
| | | 35 | | | | | 40 | | | | | 45 | | | |
| Leu | Cys | Gly | Ala | Glu | Leu | Val | Asp | Thr | Leu | Gln | Phe | Val | Cys | Gly | Glu |
| | 50 | | | | | 55 | | | | | 60 | | | | |
| Arg | Gly | Phe | Tyr | Phe | Ser | Lys | Pro | Thr | Gly | Tyr | Gly | Pro | Ser | Ser | Arg |
| 65 | | | | | 70 | | | | | 75 | | | | | 80 |
| Arg | Ser | His | Asn | Arg | Gly | Ile | Val | Asp | Glu | Cys | Cys | Phe | Gln | Ser | Cys |
| | | | | 85 | | | | | 90 | | | | | 95 | |
| Glu | Leu | Arg | Arg | Leu | Glu | Met | Tyr | Cys | Ala | Pro | Val | Lys | Ser | Gly | Lys |
| | | | 100 | | | | | 105 | | | | | 110 | | |
| Ala | Ala | Arg | Ser | Val | Arg | Ala | Gln | Arg | His | Thr | Asp | Met | Pro | Arg | Thr |
| | | 115 | | | | | 120 | | | | | 125 | | | |
| Pro | Lys | Val | Ser | Thr | Ala | Val | Gln | Ser | Val | Asp | Arg | Gly | Thr | Glu | Arg |
| | 130 | | | | | 135 | | | | | 140 | | | | |
| Arg | Thr | Ala | Gln | His | Pro | Asp | Lys | Thr | Lys | Pro | Lys | Lys | Glu | Val | His |
| 145 | | | | | 150 | | | | | 155 | | | | | 160 |
| Gln | Lys | Asn | Ser | Ser | Arg | Gly | Asn | Thr | Gly | Gly | Arg | Asn | Tyr | Arg | Met |
| | | | | 165 | | | | | 170 | | | | | 175 | |

(2) INFORMATION FOR SEQ ID NO:10:

(i) SEQUENCE CHARACTERISTICS:
        (A) LENGTH: 137 amino acids
        (B) TYPE: amino acid
        (C) STRANDEDNESS: single
        (D) TOPOLOGY: linear     (i i) MOLECULE TYPE: protein     (i x) FEATURE:
        (A) NAME/KEY: Peptide
        (B) LOCATION: 7
        (D) OTHER INFORMATION: /note="Gap of 2 after 7."

(i x) FEATURE:
        (A) NAME/KEY: Peptide
        (B) LOCATION: 31
        (D) OTHER INFORMATION: /note="Gap of 1 after 31."

(i x) FEATURE:
        (A) NAME/KEY: Peptide
        (B) LOCATION: 116
        (D) OTHER INFORMATION: /note="Gap of 27 after 116."

(x i) SEQUENCE DESCRIPTION: SEQ ID NO:10:

| Met | Ile | Thr | Pro | Thr | Val | Lys | Met | His | Thr | Met | Ser | Ser | Ser | His | Leu |
|---|---|---|---|---|---|---|---|---|---|---|---|---|---|---|---|
| 1 | | | | 5 | | | | | 10 | | | | | 15 | |
| Phe | Tyr | Leu | Ala | Leu | Cys | Leu | Leu | Thr | Phe | Thr | Ser | Ser | Ala | Thr | Ala |
| | | | 20 | | | | | 25 | | | | | 30 | | |
| Gly | Pro | Glu | Thr | Leu | Cys | Gly | Ala | Glu | Leu | Val | Asp | Ala | Leu | Gln | Phe |
| | | 35 | | | | | 40 | | | | | 45 | | | |
| Val | Cys | Gly | Asp | Arg | Gly | Phe | Tyr | Phe | Asn | Lys | Pro | Thr | Gly | Tyr | Gly |
| | 50 | | | | | 55 | | | | | 60 | | | | |
| Ser | Ser | Ser | Arg | Arg | Ala | Pro | Gln | Thr | Gly | Ile | Val | Asp | Glu | Cys | Cys |
| 65 | | | | | 70 | | | | | 75 | | | | | 80 |

```
                Phe  Arg  Ser  Cys  Asp  Leu  Arg  Arg  Leu  Glu  Met  Tyr  Cys  Ala  Pro  Leu
                                    85                       90                            95

Lys  Pro  Ala  Lys  Ser  Ala  Arg  Ser  Val  Arg  Ala  Gln  Arg  His  Thr  Asp
                               100                      105                     110

Met  Pro  Lys  Thr  Gln  Lys  Glu  Val  His  Leu  Lys  Asn  Ala  Ser  Arg  Gly
                               115                      120                     125

Ser  Ala  Gly  Asn  Lys  Asn  Tyr  Arg  Met
                     130                      135
```

( 2 ) INFORMATION FOR SEQ ID NO:11:

( i ) SEQUENCE CHARACTERISTICS:
        ( A ) LENGTH: 214 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Peptide
        ( B ) LOCATION: 44
        ( D ) OTHER INFORMATION: /note="Gap of 1 after 44."

( i x ) FEATURE:
        ( A ) NAME/KEY: Peptide
        ( B ) LOCATION: 80
        ( D ) OTHER INFORMATION: /note="Gap of 1 after 80."

( i x ) FEATURE:
        ( A ) NAME/KEY: Peptide
        ( B ) LOCATION: 111
        ( D ) OTHER INFORMATION: /note="Gap of 2 after 111."

( i x ) FEATURE:
        ( A ) NAME/KEY: Peptide
        ( B ) LOCATION: 122
        ( D ) OTHER INFORMATION: /note="Gap of 3 after 122."

( x i ) SEQUENCE DESCRIPTION: SEQ ID NO:11:

```
                Met  Glu  Thr  Gln  Lys  Arg  His  Glu  Tyr  His  Ser  Val  Cys  His  Thr  Cys
                1              5                        10                           15

Arg  Arg  Thr  Glu  Asn  Thr  Arg  Met  Lys  Val  Lys  Met  Met  Ser  Ser  Ser
                               20                       25                      30

Asn  Arg  Val  Leu  Val  Ile  Ala  Leu  Ala  Leu  Thr  Leu  Tyr  Ile  Val  Glu
                               35                       40                      45

Val  Ala  Ser  Ala  Glu  Thr  Leu  Cys  Gly  Gly  Glu  Leu  Val  Asp  Ala  Leu
                     50                       55                      60

Gln  Phe  Val  Cys  Glu  Asp  Arg  Gly  Phe  Tyr  Phe  Ser  Arg  Pro  Thr  Ser
                65                            70                      75                       80

Arg  Ser  Asn  Ser  Arg  Arg  Ser  Gln  Asn  Arg  Gly  Ile  Val  Glu  Glu  Cys
                                    85                       90                           95

Cys  Phe  Arg  Ser  Cys  Asp  Leu  Asn  Leu  Leu  Glu  Gln  Tyr  Cys  Ala  Lys
                               100                      105                     110

Pro  Ala  Lys  Ser  Glu  Arg  Asp  Val  Ser  Ala  Thr  Ser  Leu  Gln  Ile  Ile
                               115                      120                     125

Pro  Met  Val  Pro  Thr  Ile  Lys  Gln  Asp  Val  Pro  Arg  Lys  His  Val  Thr
                     130                      135                     140

Val  Lys  Tyr  Ser  Lys  Tyr  Glu  Ala  Trp  Gln  Arg  Lys  Ala  Ala  Gln  Arg
                145                           150                     155                      160

Leu  Arg  Arg  Gly  Val  Pro  Ala  Ile  Leu  Arg  Ala  Arg  Lys  Phe  Arg  Arg
                                    165                      170                          175
```

|   |   |   |   |   |   |   |   |   |   |   |   |   |   |   |
|---|---|---|---|---|---|---|---|---|---|---|---|---|---|---|
| Gln | Ala | Val | Lys<br>180 | Ile | Lys | Ala | Gln | Glu<br>185 | Gln | Ala | Met | Phe | His<br>190 | Arg | Pro |
| Leu | Ile | Thr<br>195 | Leu | Pro | Ser | Lys | Leu<br>200 | Pro | Pro | Val | Leu | Pro<br>205 | Pro | Thr | Asp |
| Asn | Tyr | Val<br>210 | Ser | His | Asn | | | | | | | | | | |

(2) INFORMATION FOR SEQ ID NO:12:

(i) SEQUENCE CHARACTERISTICS:
        (A) LENGTH: 180 amino acids
        (B) TYPE: amino acid
        (C) STRANDEDNESS: single
        (D) TOPOLOGY: linear     (ii) MOLECULE TYPE: protein     (ix) FEATURE:
        (A) NAME/KEY: Peptide
        (B) LOCATION: 57
        (D) OTHER INFORMATION: /note="Gap of 1 after 57."

(ix) FEATURE:
        (A) NAME/KEY: Peptide
        (B) LOCATION: 59
        (D) OTHER INFORMATION: /note="Gap of 1 after 59."

(ix) FEATURE:
        (A) NAME/KEY: Peptide
        (B) LOCATION: 63
        (D) OTHER INFORMATION: /note="Gap of 2 after 63."

(ix) FEATURE:
        (A) NAME/KEY: Peptide
        (B) LOCATION: 85
        (D) OTHER INFORMATION: /note="Gap of 2 after 85."

(ix) FEATURE:
        (A) NAME/KEY: Peptide
        (B) LOCATION: 96
        (D) OTHER INFORMATION: /note="Gap of 3 after 96."

(ix) FEATURE:
        (A) NAME/KEY: Peptide
        (B) LOCATION: 97
        (D) OTHER INFORMATION: /note="Gap of 8 after 97."

(ix) FEATURE:
        (A) NAME/KEY: Peptide
        (B) LOCATION: 119
        (D) OTHER INFORMATION: /note="Gap of 1 after 119."

(xi) SEQUENCE DESCRIPTION: SEQ ID NO:12:

|   |   |   |   |   |   |   |   |   |   |   |   |   |   |   |   |
|---|---|---|---|---|---|---|---|---|---|---|---|---|---|---|---|
| Met<br>1 | Gly | Ile | Pro | Met<br>5 | Gly | Lys | Ser | Met | Leu<br>10 | Val | Leu | Leu | Thr | Phe<br>15 | Leu |
| Ala | Phe | Ala | Ser<br>20 | Cys | Cys | Ile | Ala | Ala<br>25 | Tyr | Arg | Pro | Ser | Glu<br>30 | Thr | Leu |
| Cys | Gly | Gly<br>35 | Glu | Leu | Val | Asp | Thr<br>40 | Leu | Gln | Phe | Val | Cys<br>45 | Gly | Asp | Arg |
| Gly | Phe<br>50 | Tyr | Phe | Ser | Arg | Pro<br>55 | Ala | Ser | Arg | Val | Ser<br>60 | Arg | Arg | Ser | Arg |
| Gly<br>65 | Ile | Val | Glu | Glu | Cys<br>70 | Cys | Phe | Arg | Ser | Cys<br>75 | Asp | Leu | Ala | Leu | Leu<br>80 |
| Glu | Thr | Tyr | Cys | Ala<br>85 | Thr | Pro | Ala | Lys | Ser<br>90 | Glu | Arg | Asp | Val | Ser<br>95 | Thr |
| Pro | Pro | Thr | Val<br>100 | Leu | Pro | Asp | Asn | Phe<br>105 | Pro | Arg | Tyr | Pro | Val<br>110 | Gly | Lys |
| Phe | Phe | Gln | Tyr | Asp | Thr | Trp | Lys | Gln | Ser | Thr | Gln | Arg | Leu | Arg | Arg |

|     |     |     |     |     |     |     | 115 |     |     |     | 120 |     |     |     | 125 |     |     |     |
| --- | --- | --- | --- | --- | --- | --- | --- | --- | --- | --- | --- | --- | --- | --- | --- | --- | --- | --- |
| Gly | Leu | Pro | Ala | Leu | Leu | Arg | Ala | Arg | Arg | Gly | His | Val | Leu | Ala | Lys |
|     | 130 |     |     |     |     | 135 |     |     |     |     | 140 |     |     |     |     |
| Glu | Leu | Glu | Ala | Phe | Arg | Glu | Ala | Lys | Arg | His | Arg | Pro | Leu | Ile | Ala |
| 145 |     |     |     |     | 150 |     |     |     |     | 155 |     |     |     |     | 160 |
| Leu | Pro | Thr | Gln | Asp | Pro | Ala | His | Gly | Gly | Ala | Pro | Pro | Glu | Met | Ala |
|     |     |     |     | 165 |     |     |     |     | 170 |     |     |     |     | 175 |     |
| Ser | Asn | Arg | Lys |
|     |     |     | 180 |